(12) United States Patent
Gohl

(10) Patent No.: US 6,704,958 B2
(45) Date of Patent: Mar. 16, 2004

(54) PILLOW, ESPECIALLY FOR USE DURING THERAPEUTIC MEASURES

(76) Inventor: Hartmut E. Gohl, An der Gumpgesbrucke 15, Haarst (DE), D-41564

(*) Notice: Subject to any disclaimer, the term of this patent is extended or adjusted under 35 U.S.C. 154(b) by 0 days.

(21) Appl. No.: 10/332,277

(22) PCT Filed: May 3, 2002

(86) PCT No.: PCT/EP02/04885
§ 371 (c)(1),
(2), (4) Date: Jan. 7, 2003

(87) PCT Pub. No.: WO02/089905
PCT Pub. Date: Nov. 14, 2002

(65) Prior Publication Data
US 2003/0177582 A1 Sep. 25, 2003

(30) Foreign Application Priority Data
May 7, 2001 (DE) .................... 201 07 734 U

(51) Int. Cl.⁷ .................................. A47G 9/00
(52) U.S. Cl. ................................ 5/639; 5/904
(58) Field of Search .............. 5/639, 636, 640, 5/643, 904

(56) References Cited

U.S. PATENT DOCUMENTS

| | | |
|---|---|---|
| 2,958,769 A | 11/1960 | Bounds |
| 3,290,450 A | 12/1966 | Majoros |
| 3,384,719 A * | 5/1968 | Lanzara .................. 5/904 X |
| 3,621,155 A * | 11/1971 | Pruitt ..................... 5/639 X |
| 4,038,499 A * | 7/1977 | Yeaple ................... 381/301 |
| 4,782,533 A | 11/1988 | Haynie |
| 4,862,438 A * | 8/1989 | Fry ......................... 5/904 X |
| 5,063,912 A * | 11/1991 | Hughes ................... 5/904 X |
| 5,123,133 A * | 6/1992 | Albert ..................... 5/639 |
| 5,201,002 A * | 4/1993 | Dahlem ................... 5/639 X |
| 5,313,678 A | 5/1994 | Redewill |
| 5,479,667 A | 1/1996 | Nelson et al. |
| 5,682,633 A * | 11/1997 | Davis ...................... 5/636 |
| 5,926,879 A * | 7/1999 | Davis ...................... 5/636 |
| 6,202,232 B1 * | 3/2001 | Andrei .................... 5/636 |

FOREIGN PATENT DOCUMENTS

| | | | |
|---|---|---|---|
| DE | G9410690.8 | 11/1994 | |
| GB | 2113502 A * | 8/1983 | ........ 5/639 |
| WO | WO 99/21460 | 5/1999 | |
| WO | WO 99/58088 | 11/1999 | |

* cited by examiner

Primary Examiner—Robert G. Santos
(74) Attorney, Agent, or Firm—Liniak, Berenato & White, LLC

(57) ABSTRACT

The invention concerns a pillow, in particular for use in the context of therapeutic measures, having a pillow body (2), made of an elastically deformable material, in which several loudspeakers (9) can be positioned and which forms a support surface (3) on its upper side, which is characterized in that the loudspeakers (9) are retained in a rail (8) made of an elastically deformable material, and the rail (8) is detachably inserted into a corresponding recess (7) on the underside of the pillow body (2).

13 Claims, 3 Drawing Sheets

PILLOW, ESPECIALLY FOR USE DURING THERAPEUTIC MEASURES

The present invention concerns a pillow, in particular for use in the context of therapeutic measures, having a pillow body, made of an elastically deformable material, in which several loudspeakers can be positioned and which forms a support surface on its upper side.

Pillows of this kind with built-in loudspeakers are known from WO 99/58088 and are utilized principally to treat auditory disorders, for example tinnitus aurium, using so-called music therapies, pieces of music that are superimposed on the audible noise subjectively perceived by the tinnitus patient being played to the patient in accordance with the auditory disturbance.

The use of such music-therapy pillows has proven entirely successful in the context of this treatment of tinnitus disorders or other sleep disturbances. The fact that the pillows either cannot be cleaned at all or can be cleaned only after laborious disassembly of the components of the loudspeaker system, and moreover that individual positioning of the loudspeakers as the patient wishes involves considerable effort, is nevertheless perceived as disadvantageous.

It is therefore the object of the invention to configure a pillow of the kind cited initially in such a way that the pillow can easily be cleaned, and in particular so that the loudspeakers can also be positioned in simple fashion.

According to the present invention, this object is achieved in that the loudspeakers are retained in a rail made of an elastically deformable material, and the rail is detachably inserted into a corresponding recess on the underside of the pillow body.

According to the present invention, the loudspeakers are therefore no longer, as in the existing art, inserted directly into the pillow body, but rather are preassembled on a rail, and thus can easily be mounted on the pillow body or detached therefrom for cleaning of the pillow body, by the fact that the rail is inserted into the recess provided therefor on the underside of the pillow body or removed again therefrom.

The rail advantageously has cutouts, in particular in the form of through openings that can be produced particularly easily, into which the loudspeakers are inserted. According to a preferred embodiment, the loudspeaker cutouts are provided in the axial end regions of the rail so that the loudspeakers positioned therein are placed as far apart as possible from one another and, in particular, on either side of a head resting on the pillow. The best possible acoustic effect is thereby achieved.

If the pillow body is orthopedically shaped, it may also be advisable to provide the recess for the rail on the underside of the pillow in the neck region of the pillow, where a neck ridge is usually located. The patient then hears not only via the ears but also through the so-called auditory bones.

According to a preferred embodiment of the invention, provision is made for the pillow body and the rail each to be made of foam material, so that the rail can easily be inserted into the corresponding recess of the pillow body and removed again therefrom. With appropriate dimensioning the rail then retains itself in the recess so that no additional attachment elements, for example hook-and-loop straps or the like, are necessary for mounting the rail on the pillow body. In the same fashion, the loudspeakers can be easily and securely positioned in the cutout. It has proven advantageous if the rail is, in this context, made at least for the most part of a hard foam material, thereby giving the rail a certain strength. So as not thereby to impair comfort for the user, in a further development of this embodiment provision is made for the rail to have on its upper side, in the region between the loudspeaker cutouts provided in the end regions of the rail, a recess into which is inserted a foam strip made of an elastically deformable material that is softer than the hard foam material and preferably is made of the material of the pillow body.

According to a further embodiment of the invention, provision is made for the loudspeakers to be arranged on the rail adjustably in the longitudinal rail direction. This embodiment makes it possible to adapt the loudspeaker position individually to the user's head shape. It is additionally advantageous if, in particular, slit-shaped through openings for the necessary supply and/or transmission cables are provided in the rail.

A further advantageous embodiment of the invention comprises a pillow cover, embodied in particular as a replaceable cover, that can easily be cleaned when necessary. Openings through which the supply and/or transmission cables for the loudspeakers can be guided are then provided in the pillow cover, advantageously on the pillow underside near the mutually opposite transverse sides. The arrangement of openings on both transverse sides and, in particular, at the corner regions of the cushion makes it possible to position the cables in an unobtrusive manner depending on whether the patient sleeps on his or her right or left side.

Regarding further advantageous embodiments of the invention, reference is made to the dependent claims and to the description below of an exemplary embodiment referring to the attached drawings, in which:

Figure 1:
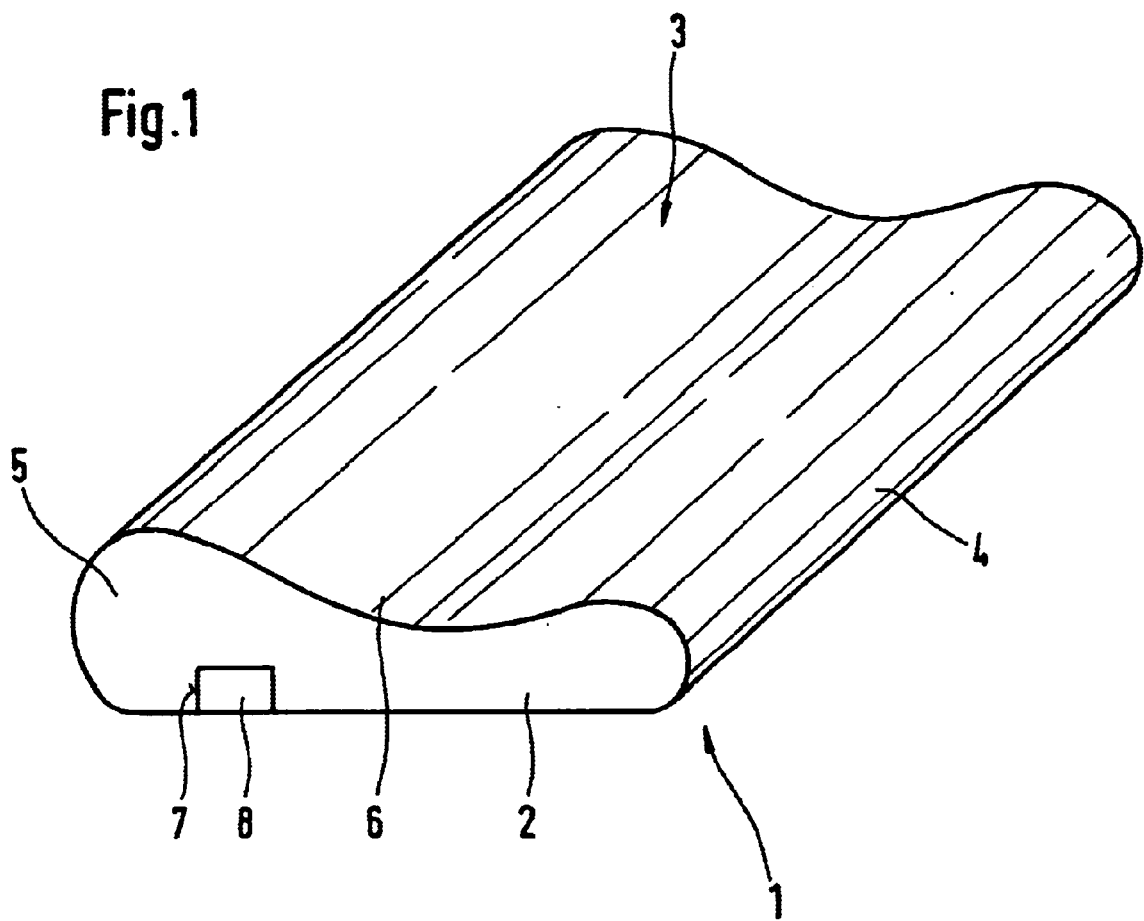
FIG. 1 shows an embodiment of a pillow according to the present invention in a schematic perspective view.
Figure 2:
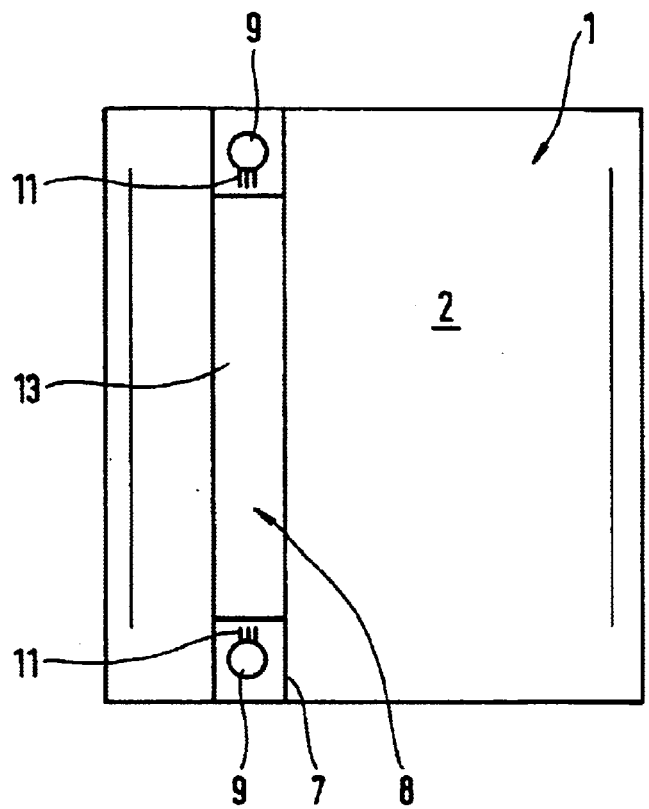
FIG. 2 shows the pillow of FIG. 1 in a view from below.
Figure 3:
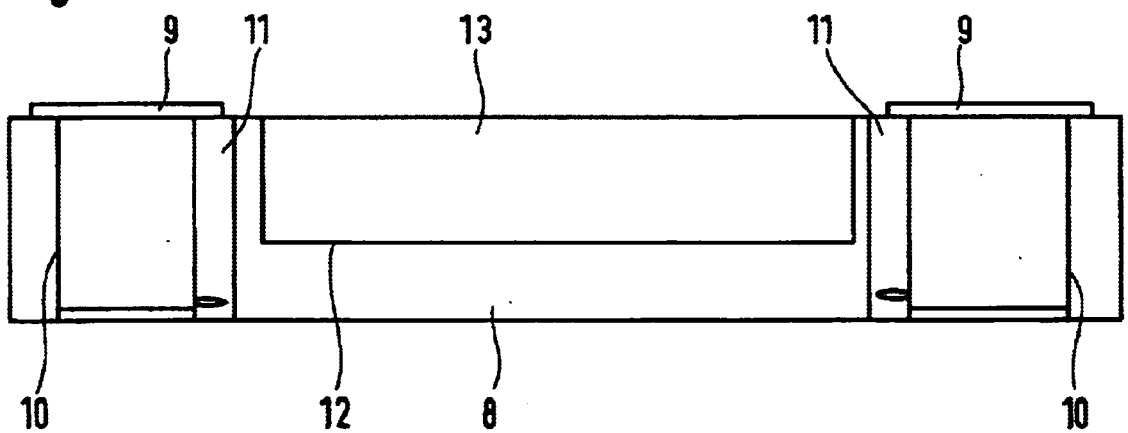
FIG. 3 shows the pillow's rail in a front view.

FIGS. 1 and 2 depict a music-therapy pillow 1 according to the present invention that can be used in particular for the treatment of tinnitus disorders. The pillow possesses a pillow body 2 of basically rectangular shape made of a washable elastic foam material that has on its upper side an orthopedically shaped support surface 3 having a smaller neck ridge 4 running along one longitudinal side, a larger ridge 5 running along the other longitudinal side, and a trough 6 lying therebetween.

A recess 7 of approximately rectangular cross section, which extends over the entire length of pillow body 2, is provided on the underside of pillow body 3 in the transition region between thick ridge 5 and trough 6. Inserted into this recess 7 is a rail 8 in which a loudspeaker system, which in the present case comprises two active loudspeakers 9, is received. Respective through openings 10, into which loudspeakers 9 are inserted, are provided for this purpose in the regions of rail 8. Proceeding from these through openings 10 are cable slits 11, also passing through, in which the loudspeaker terminals and the supply cables (not depicted) for loudspeakers 9 are positioned.

Rail 8 is made of a hard foam material, so that it possesses sufficient stability and furthermore so that loudspeakers 9 are retained in through openings 10 without additional fastening means, for example adhesive strips. The use of a rail made of foam furthermore has the advantage that with appropriate dimensioning, rail 8 retains itself in recess 7 of pillow body 2 and does not need to be immobilized by way of adhesive tapes, hook-and-loop straps, or the like, even though such additional attachment means can be provided for safety's sake.

A recess 12, into which is inserted a foam strip 13 of the same material of which pillow body 2 is also made, is provided in the upper side of rail 8 between the end regions in which through openings 10 for loudspeakers 9 are provided. The result of this is that the harder material of rail 8 has little or no influence on sleeping comfort.

Figure 4:
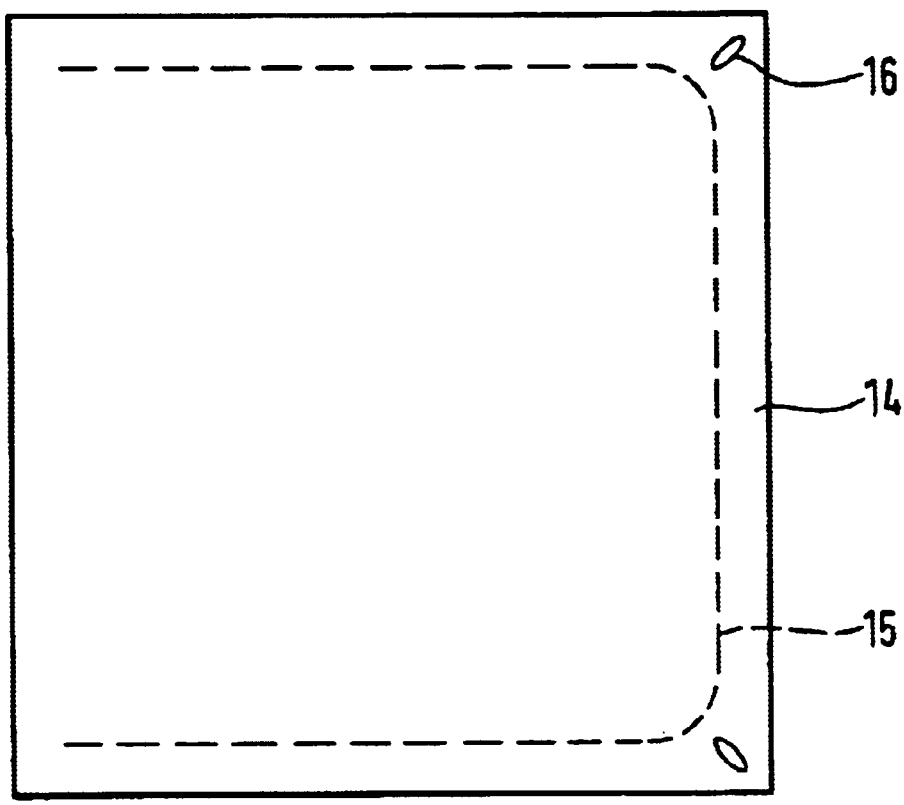
FIG. 4 shows a pillow cover for the pillow in a view from below.

FIG. 4 depicts a pillow cover for pillow 1. This pillow cover 14 is made of a washable material and possesses on its underside a schematically indicated zipper closure 15 so that it can be pulled off pillow body 12 and thereby easily cleaned. In the corners close to the neck region, pillow cover 14 possesses two openings 16 through which connector cables for loudspeakers 9 can be guided. Openings 16 are provided in both corner regions so that the user can selectably guide the connector cables through one or the other opening 16, depending on whether he or she lies on the left or right side when sleeping.

Cleaning of the pillow body is very simple according to the present invention, since once pillow cover 14 has been pulled off, loudspeakers 9 with rail 8 can easily be removed.

What is claimed is:

1. A pillow, in particular for use in the context of therapeutic measures, having a pillow body (2), made of an elastically deformable material, in which several loudspeakers (9) can be positioned and which forms a support surface (3) on its upper side,
    wherein the loudspeakers (9) are retained in a rail (8) made of an elastically deformable material, and the rail (8) is detachably inserted into a corresponding recess (7) on the underside of the pillow body (2).

2. The pillow as defined in claim 1, wherein the rail (8) has cutouts (10), in particular in the form of through openings, into which the loudspeakers (9) are inserted.

3. The pillow as defined in claim 2, wherein the loudspeaker cutouts (10) are provided in the axial end regions of the rail (8).

4. The pillow as defined in claim 1, wherein the rail (8) is made at least for the most part of hard foam.

5. The pillow as defined in claim 3, wherein the rail (8) has on its upper side, in the region between the loudspeaker cutouts (10), a recess (12) into which is inserted a foam strip (13) made of an elastically deformable material that is softer than the hard foam material.

6. The pillow as defined in claim 1, wherein the loudspeakers (9) are arranged on the rail (8) adjustably in the longitudinal rail direction.

7. The pillow as defined in claim 1, wherein through openings (11), in particular slit-shaped, for cables are provided in the rail (8).

8. The pillow as defined in claim 1, wherein the pillow body (2) is orthopedically shaped.

9. The pillow as defined in claim 1, wherein the pillow body (2) possesses a neck ridge (4), and the recess (7) for the rail (8) is provided on the underside of the pillow in the region of said neck ridge (4).

10. The pillow as defined in claim 1, wherein the pillow body (2) is made of a foam material.

11. The pillow as defined in claim 10, wherein the foam material is washable.

12. The pillow as defined in claim 1, wherein a pillow cover (14) is provided.

13. The pillow as defined in claim 12, wherein the pillow cover (14) has openings (16) on the pillow underside, near the opposite transverse sides, through which supply and/or transmission cables for the loudspeakers (9) can be guided.

* * * * *